United States Patent
Finarov et al.

(10) Patent No.: US 7,330,259 B2
(45) Date of Patent: Feb. 12, 2008

(54) OPTICAL MEASUREMENTS OF PATTERNED ARTICLES

(75) Inventors: Moshe Finarov, Rehovot (IL); Shahar Gov, Rehovot (IL)

(73) Assignee: Nova Measuring Instruments Ltd., Rehovot (IL)

(*) Notice: Subject to any disclaimer, the term of this patent is extended or adjusted under 35 U.S.C. 154(b) by 372 days.

(21) Appl. No.: 11/002,988

(22) Filed: Dec. 3, 2004

(65) Prior Publication Data
US 2005/0264801 A1    Dec. 1, 2005

(30) Foreign Application Priority Data
May 27, 2004 (IL) .................................. 162199

(51) Int. Cl.
G01J 4/00 (2006.01)
G01N 21/88 (2006.01)

(52) U.S. Cl. .................. 356/369; 356/365; 250/225

(58) Field of Classification Search .. 356/237.1–237.5, 356/364–69, 630; 250/225, 559.4
See application file for complete search history.

(56) References Cited

U.S. PATENT DOCUMENTS

| | | | | |
|---|---|---|---|---|
| 5,042,951 A * | 8/1991 | Gold et al. | | 356/369 |
| 5,181,080 A * | 1/1993 | Fanton et al. | | 356/632 |
| 5,333,052 A * | 7/1994 | Finarov | | 356/369 |
| 5,373,359 A * | 12/1994 | Fujimoto | | 356/328 |
| 5,450,201 A * | 9/1995 | Katzir et al. | | 356/369 |
| 6,281,974 B1 * | 8/2001 | Scheiner et al. | | 356/491 |
| 6,483,580 B1 * | 11/2002 | Xu et al. | | 356/300 |
| 6,657,736 B1 * | 12/2003 | Finarov et al. | | 356/625 |
| 6,665,070 B1 | 12/2003 | Yarussi et al. | | |
| 6,721,052 B2 * | 4/2004 | Zhao et al. | | 356/369 |
| 6,734,967 B1 | 5/2004 | Piwonka-Corle et al. | | |
| 6,867,862 B2 | 3/2005 | Nikoonahad | | |
| 7,061,561 B2 * | 6/2006 | Silverstein et al. | | 349/117 |
| 7,115,858 B1 * | 10/2006 | Holden et al. | | 250/225 |

FOREIGN PATENT DOCUMENTS

| | | |
|---|---|---|
| EP | 0 610 945 A1 | 8/1994 |
| JP | 2102404 | 4/1990 |
| WO | WO-02/079780 A2 | 10/2002 |

OTHER PUBLICATIONS

Coulombe, Stephen A. "Scatterometry measurement of sub-0.1 μm linewidth gratings" J. Vac. Sci. Technol. B (Jan./Feb. 1998) vol. 16, No. 1, pp. 80-87.

Minhas, Babar K. "Ellipsometric scatterometry for the metrology of sub-0.1-μm-linewidth structures" Applied Optics (Aug. 1998) vol. 37, No. 22, pp. 5112-5115.

* cited by examiner

Primary Examiner—Sang H. Nguyen
(74) Attorney, Agent, or Firm—Browdy and Neimark, PLLC (57) ABSTRACT

A method and system are presented for use in measuring/inspecting a patterned article. Optical measurements are applied to a measurement site on the article by illuminating the measurement site with a plurality of wavelengths at substantially normal incidence of the illuminating light, detecting light returned from the illuminated site, and generating measured data indicative thereof. The measurements are applied to the measurement site through a polarizer rotatable between its different orientations selected from a number of pre-calibrated orientations.

37 Claims, 9 Drawing Sheets

| Grating angle range [Deg] $\alpha$ | Best triplet out of $\beta$ [0,65.2,90.4,116.8] |
|---|---|
| $0 + 90n < \alpha \leq 2 + 90n$ | [0,65.2,90.4,116.8] |
| $2 + 90n < \alpha \leq 13 + 90n$ | [0,65.2,90.4] |
| $13 + 90n < \alpha \leq 27 + 90n$ | [0,65.2,116.8] |
| $27 + 90n < \alpha \leq 32 + 90n$ | [0,90.4,116.8] |
| $32 + 90n < \alpha \leq 58 + 90n$ | [65.2,90.4,116.8] |
| $58 + 90n < \alpha \leq 63 + 90n$ | [0,65.2,90.4] |
| $63 + 90n < \alpha \leq 77 + 90n$ | [0,65.2,116.8] |
| $77 + 90n < \alpha \leq 90 + 90n$ | [0,90.4,116.8] |

Where n=1,2,3,4.

The algorithm of selection in this case can be written in the following form:

| Grating angle range [Deg] $\alpha$ | Best triplet out of [0,60,90,120] $\beta$ |
|---|---|
| $-1+90n < \alpha \leq 15+90n$ | {0,60,90} |
| $15+90n < \alpha \leq 25+90n$ | {0,60,120} |
| $25+90n < \alpha \leq 31+90n$ | {0,90,120} |
| $31+90n < \alpha \leq 44+90n$ | {60,90,120} |
| $44+90n < \alpha \leq 46+90n$ | {0,60,120} |
| $46+90n < \alpha \leq 60+90n$ | {60,90,120} |
| $60+90n < \alpha \leq 64+90n$ | {0,60,90} |
| $64+90n < \alpha \leq 74+90n$ | {0,60,120} |
| $74+90n < \alpha \leq 89+90n$ | {0,90,120} |

Where n=1,2,3,4.

OPTICAL MEASUREMENTS OF PATTERNED ARTICLES

FIELD OF THE INVENTION

This invention relates in general to the field of optical measurements/inspection, and particularly relates to measurement/inspection of patterned articles.

BACKGROUND OF THE INVENTION

It is known that polarized normal incidence spectrometry may be used for measuring line profiles' parameters being applied to one-dimensional (1D) line arrays (pattern) on an article by help of Rigorous Coupled-wave Theory (Further below RCWT) and the like modeling. The same approach can also be applied to two-dimensional (2D) line arrays or any other 2D periodic pattern (e.g. arrays of lines, pads, vias, etc.).

U.S. Pat. No. 6,665,070 discloses a metrology device with a rotatable polarizer that is calibrated to align the transmission axis of the polarizer with the axis of orientation of a sample, such as a diffraction grating. The axis of orientation of the diffraction grating can be either the TE or TM axis. The system offset angle between the transmission axis of the polarizer in its home position and an axis of motion of the stage, such as a polar coordinate stage, is determined. Whenever a new substrate is loaded onto the stage, the sample offset angle between the axis of motion of the stage and the axis of orientation of a sample is measured. The polarizer offset angle, which is the angle between transmission axis of the polarizer and the axis of orientation of the sample, is the sum of the system offset angle and the sample offset angle. Thus, by rotating the polarizer by an amount equivalent to the sum of the system offset angle and the sample offset angle, the polarizer offset angle is reduced to zero. If desired, the polarizer may be rotated once to compensate for the system offset angle and then rotated to compensate for the sample offset angle for each newly loaded substrate or the polarizer may be rotated to compensate for both the system offset angle and the sample offset angle for each newly loaded substrate.

U.S. Pat. No. 6,657,736 discloses a method and system for determining a line profile in a patterned structure, aimed at controlling a process of manufacture of the structure. The patterned structure comprises a plurality of different layers, the pattern in the structure being formed by patterned regions and un-patterned regions. At least first and second measurements are carried out, each utilizing illumination of the structure with a broad wavelengths band of incident light directed on the structure at a certain angle of incidence, detection of spectral characteristics of light returned from the structure, and generation of measured data representative thereof. The measured data obtained with the first measurement is analyzed, and at least one parameter of the structure is thereby determined. Then, this determined parameter is utilized, while analyzing the measured data obtained with the second measurements enabling the determination of the profile of the structure.

According to the techniques of these patents, measurement of TE and TM polarization components is used that require a certain specific orientation of the polarizer's axis relative to the orientation of the line arrays on a patterned article. Usually, the polarizer's axis is orientated parallel to the line (TE polarization measurement) and/or perpendicular to the line (TM measurements).

SUMMARY OF THE INVENTION

There is a need in the art to facilitate polarization-based measurements on patterned structures, by providing a novel measurement system and method.

The main idea of the present invention is associated with the following. As indicated above, the prior art techniques utilize measurements of TE and TM polarization components requiring a certain specific orientation of the polarizer's axis relative to the orientation of the line arrays on a patterned article. If an article under measurements is positioned on a movable X,Y-stage, it is sufficient to align the article relative to coordinate system of the stage, so a pre-aligned polarizer can be used at two predefined positions relative to the stage coordinates. If R-θ stage is used, it is necessary to align the polarizer to the article on the stage in each orientation of the article. This technique suffers from drawbacks associated with the following:

Since an optical system induces some polarization and intensity change, it is necessary to calibrate the efficiency of the optical system for each orientation of the polarizer. Since the time acceptable for such calibration is never infinite, practically calibration is carried out at a limited number of angles of polarization. Based on such a sampling, the efficiency of the optical system for any angle is calculated by interpolating calibrated values at sampled angles, thus unavoidably inducing an additional source of measurement error. Another drawback of the above technique relates to the optical axis deviation caused by the polarizer rotation. If the optical axis of the polarizer (e.g., Glan-Thompson prisms based polarizer) does not coincide perfectly with the rotation axis (which is always the case), an optical beam that passes the polarizer is deflected and therefore impinges the measured article slightly aside the nominal coordinates. Such a deflection is a function of the angle of the polarizer's axis relative to its zero-position. It is thus clear that if the polarizer is to be aligned to an arbitrary positioned grating (the orientation of a patterned article), such a deflection should be pre-calibrated (with associated interpolation) and taken into account in positioning the article. This is another source of calibrating error that is caused by the polarizer rotation in the full range of possible orientations (±90°).

Yet another common drawback of the prior art measurement techniques is that they do not exploit all the information that may be obtained from the sample, but use only the amplitude of diffraction efficiency for TE and TM polarization states. Valuable information about a phase shift between these two polarization states in such case is ignored.

The present invention solves the above problems by measuring in a patterned article with at least three polarization states of incident light. This technique takes into account a phase difference between the TE and TM polarizations. It is known that this phase difference may be obtained by taking measurement in at least one additional orientation of a polarizer relative to a grating. Usually, from the symmetry point of view, a 45° angle is selected. Use of more angles does not provide independent measurements but may be useful for reducing measurement errors. So, by measuring with at least three polarization states, it is possible to measure both the amplitude of the diffraction efficiency for each polarization state and the phase shift between the polarization states.

There is thus provided according to one aspect of the invention, a method for use in measuring/inspecting a patterned article, the method comprising applying optical measurements to a measurement site on the article by illuminating the measurement site with a plurality of wavelengths at substantially normal incidence of the illuminating light, detecting light returned from the illuminated site, and generating measured data indicative thereof, wherein the measurements are applied to the measurement site through a polarizer rotatable between its different orientations selected from a number of pre-calibrated orientations.

The method utilizes calibration data indicative of an angular orientation $\phi$ of the pattern on the article under measurements and the selected polarization.

Preferably, these three selected polarization states include two mutually perpendicular polarizations corresponding to the angular orientations $\phi$ and $(90+\phi)$, and at least one intermediate polarization state corresponding to the polarization vector orientation in between these mutually perpendicular polarization states. The intermediate polarization may for example correspond to a 45° angular orientation. Considering four selected polarizations, the three polarization states are selected as those corresponding to the orientations closest to the given orientation of the pattern on the article under measurements.

The measured data is processed to determine diffraction efficiencies $R_{TE}$ and $R_{TM}$ for, respectively, linear polarization states of the illuminating light relative to the pattern on the article under measurements, and a phase shift between them, thereby enabling calculation of a diffraction efficiency $R(\phi)$ for any angular orientation $\phi$ of the polarizer relative to the pattern.

According to another aspect of the invention there is provided a method for use in measuring/inspecting a patterned article, the method comprising applying optical measurements to a measurement site on the article by illuminating the measurement site with a plurality of wavelengths at substantially normal incidence of the illuminating light, detecting light returned from the illuminated site, and generating measured data indicative thereof, wherein the measurements are applied to the measurement site through a polarizer, rotatable between its different orientations, with at least three different orientations of the polarizer selected from at least four pre-calibrated orientations of the polarizer.

According to yet another aspect of the invention, there is provided a method for use in measuring/inspecting a patterned article, the method comprising applying optical measurements to a measurement site on the article by illuminating the measurement site with a plurality of wavelengths at substantially normal incidence of the illuminating light, detecting light returned from the illuminated site, and generating measured data indicative thereof, wherein the measurements are applied to the measurement site through a polarizer rotatable between its different orientations selected from a number of pre-calibrated orientations, data being provided about an angular orientation a of the pattern on the article under measurements with respect to a selected zero position of the polarizer.

According to yet another aspect of the invention, there is provided a system for use in measuring/inspecting a patterned article, the system comprising:

an illumination assembly configured and operated for producing illuminating light of a plurality of wavelengths;

a detection assembly comprising a spectrometer for receiving light of different wavelengths and generating measured data indicative thereof;

a light directing assembly configured for directing the illuminating light onto the article along an axis substantially perpendicular to the article and collecting light returned from the article along said axis and directing the collected light to the detection assembly, the light directing assembly comprising a polarizer assembly operated to be rotatable between its different orientations; and a control unit operable for receiving and processing the measured data, the control unit utilizing calibrated data indicative of an angular orientation $\phi$ of the pattern on the article under measurements and at least three pre-calibrated orientations of the polarizer, to thereby select the different polarizer orientations for measurements on each measurement site.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
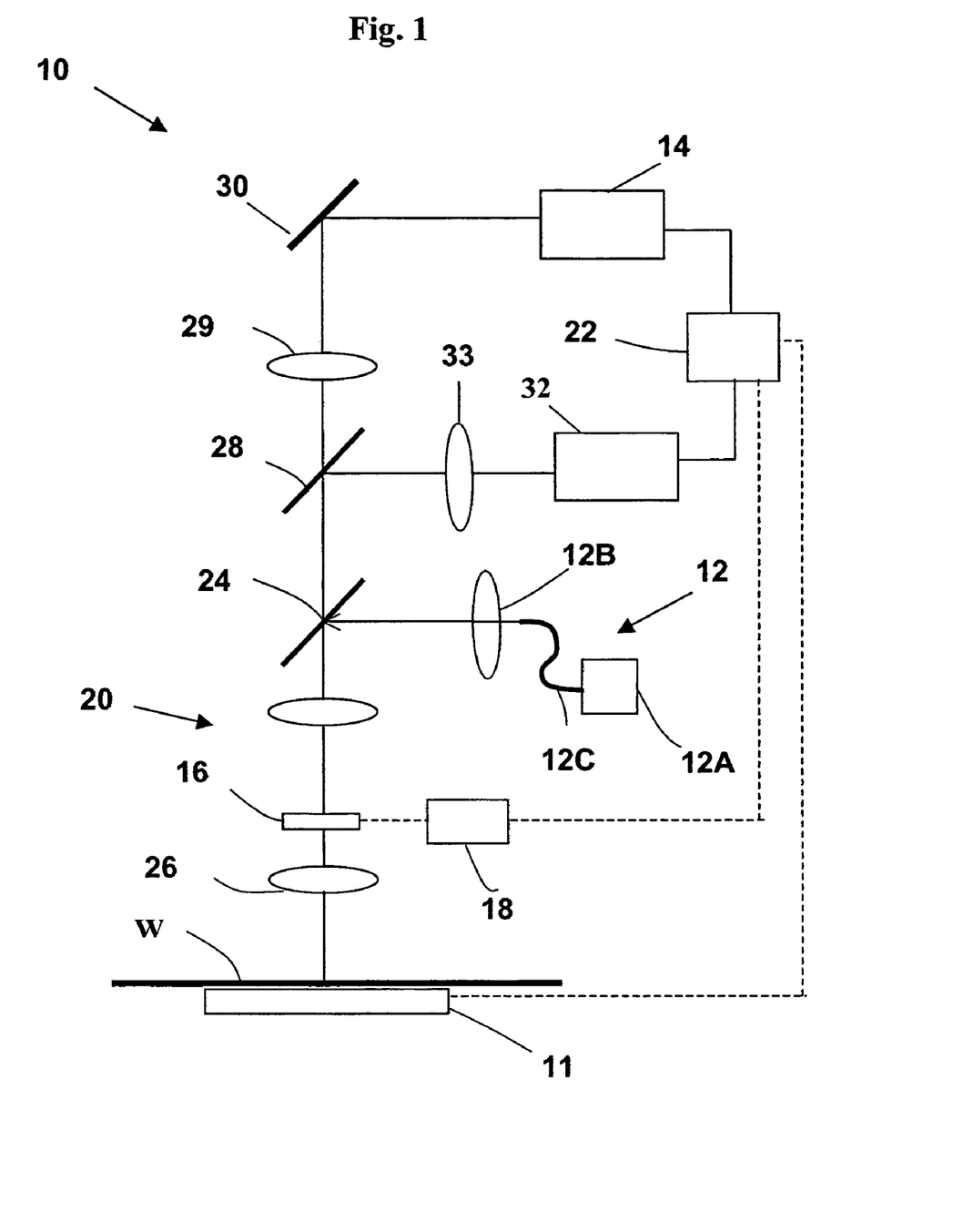
FIG. 1 is a schematic illustration of an optical system suitable to be used in the present invention.

Referring to FIG. 1, there is schematically illustrated an optical system 10 for inspecting/measuring in a patterned article such as semiconductor wafer W actually presenting a grating (e.g., array of lines) on a substrate. The wafer is located on a stage 11, which is preferably configured for rotation and back and forward movement along at least one axis (the R-Theta stage).

The system 10 is configured as a normal incidence polarized reflectance spectrometer, and includes a light source assembly 12; a detector assembly 14 including a spectrometer; a polarizer assembly 16 associated with a drive 18 that is operated to vary the orientation of the preferred polarization of the polarizer with respect to the orientation of the grating; a light directing assembly 20; and a control unit 22 that receives and interprets measured data coming from the detector assembly. The light source assembly 12 includes at least one light emitting element 12A and optionally includes a condenser lens arrangement 12B, as well as a fiber 12C through which light may be conveyed from the remote light emitter element(s). The light source assembly is configured for producing light of different wavelengths, which may be achieved by using different light emitting elements or a broadband illuminator. The light directing assembly 20 includes a beam splitter 24 accommodated in an optical path of light coming from the light source 12 to reflect it towards the wafer W and in the optical path of reflected light coming from the wafer to transmit the reflected light towards the detector 14; a focusing/collecting lens arrangement 26; a pinhole mirror 28 for transmitting a part of collected light to the detector 14 via a relay lens 29 and possibly another mirror 30 and for reflecting the other part of the collected light towards an imaging assembly 32 via an imaging lens 33. The polarizer 16 is operated by the control unit 22 to provide predetermined orientation of the preferred plane of polarization.

It should be noted that the pinhole mirror 28 works as a beam separator between the measurement path propagating toward the detector 14 and an imaging path propagating toward the imaging assembly 32 (e.g. CCD camera); however other beam separator may be used instead of the pinhole mirror, for example a beam splitter, switching mirror, etc.

Figure 2:
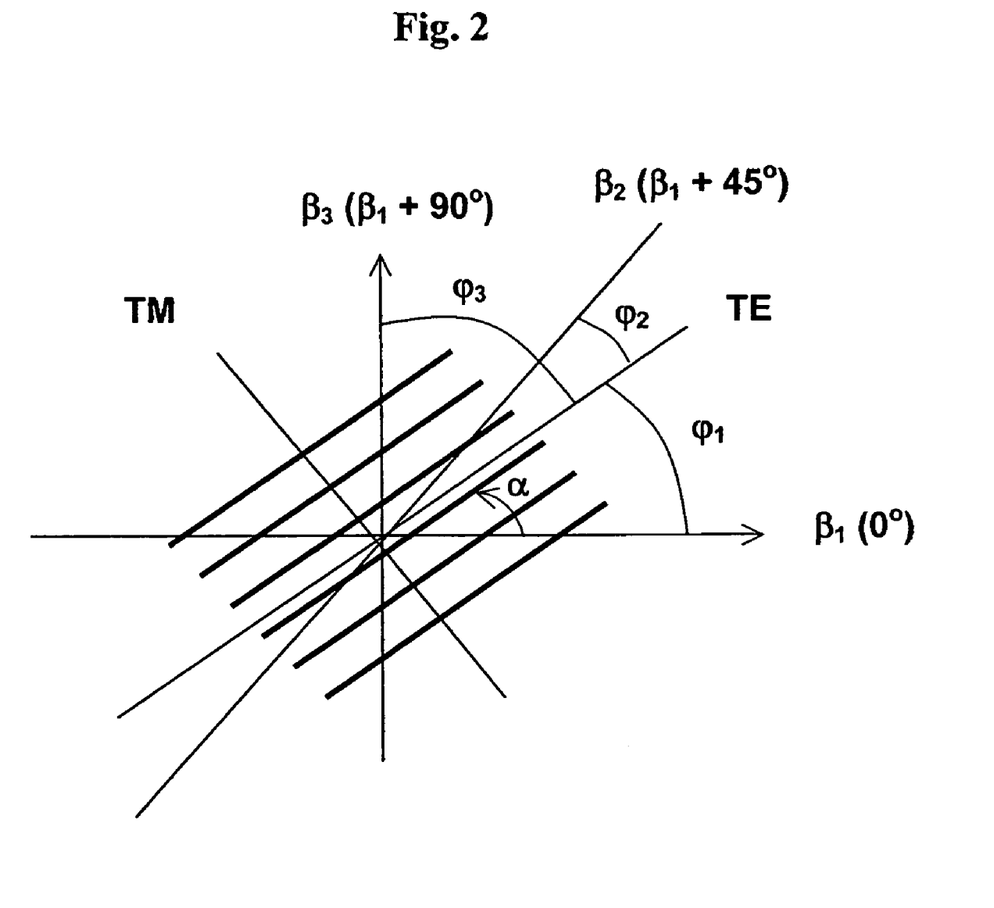
FIG. 2 illustrates the principles of the present invention.

Reference is made to FIG. 2 illustrating the principles of the present invention. Generally, during the measurements the polarizer is positioned with any angular orientation $\phi_i$ relative to the grating under measurements. Considering $\beta_1$ as the zero-angle polarization position ($\beta_1$=0), $\phi$=$\alpha$, wherein $\alpha$ is an angle between the line array axis (grating) and the zero-angle polarizer position $\beta_1$. In general case, when $\beta_1 \neq 0$, the angular orientation $\phi_i$ relative to the grating under measurements could be defined as $\phi_i=\beta_i-\alpha$. Diffraction efficiency R($\phi$) for any angular orientation $\phi_i$ can be calculated by the following equation:

$$R(\phi) = R_{TE} \cdot \cos^4 \phi + R_{TM} \cdot \sin^4 \phi + 2\sqrt{R_{TE} \cdot R_{TM}} \cdot \cos \delta \cdot \sin^2 \phi \cdot \cos^2 \phi \quad (1)$$

In order to determine three independent parameters—$R_{TE}$, $R_{TM}$ and cos $\delta$ (phase shift between TE and TM polarizations), that should be compared to the theoretical calculated data, it is needed to measure diffraction efficiency on at least three different angles, $\phi_1$, $\phi_2$ and $\phi_3$, corresponding to three fixed polarizer positions $\beta_1$, $\beta_2$ and $\beta_3$ and to solve the following system of equations:

$$\begin{cases} R(\varphi_1) = R_{TE} \cdot \cos^4 \varphi_1 + R_{TM} \cdot \sin^4 \varphi_1 + 2\sqrt{R_{TE} \cdot R_{TM}} \cdot \cos\delta \cdot \sin^2 \varphi_1 \cdot \cos^2 \varphi_1 \\ R(\varphi_2) = R_{TE} \cdot \cos^4 \varphi_2 + R_{TM} \cdot \sin^4 \varphi_2 + 2\sqrt{R_{TE} \cdot R_{TM}} \cdot \cos\delta \cdot \sin^2 \varphi_2 \cdot \cos^2 \varphi_2 \\ R(\varphi_3) = R_{TE} \cdot \cos^4 \varphi_3 + R_{TM} \cdot \sin^4 \varphi_3 + 2\sqrt{R_{TE} \cdot R_{TM}} \cdot \cos\delta \cdot \sin^2 \varphi_3 \cdot \cos^2 \varphi_3 \end{cases} \quad (2)$$

which may be rewritten in matrix form as:

$$\begin{pmatrix} R(\varphi_1) \\ R(\varphi_2) \\ R(\varphi_3) \end{pmatrix} = \underbrace{\begin{pmatrix} \cos^4 \varphi_1 & \sin^4 \varphi_1 & \sin^2 \varphi_1 \cos^2 \varphi_1 \\ \cos^4 \varphi_2 & \sin^4 \varphi_2 & \sin^2 \varphi_2 \cos^2 \varphi_2 \\ \cos^4 \varphi_3 & \sin^4 \varphi_3 & \sin^2 \varphi_3 \cos^2 \varphi_3 \end{pmatrix}}_{A} \begin{pmatrix} R_{TE} \\ R_{TM} \\ 2\sqrt{R_{TE} R_{TM}} \cos\delta \end{pmatrix} \quad (3)$$

wherein the matrix of coefficients will be denoted by A.

Here, A is a three-by-three matrix, which depends on three polarizer orientations selected for measurements.

In these linear equations, the unknowns are $R_{TE}$, $R_{TM}$ and cos $\delta$, while the known parameters are $\phi_{1,2,3}$ and R($\phi_{1,2,3}$). After determining the unknown parameters, they are compared to a theoretical model, as will be described further below with reference to FIG. 8. Alternatively, the output of the theoretical model is first transformed into R($\phi_{1,2,3}$) and then compared to the measurements, as will be described further below with reference to FIG. 9.

So, it is possible, in principle, to keep an actual measurement position $\beta_i$ of the polarizer constant, e.g., 0°, 90° or 45°, for determining the diffraction efficiency R for each orientation $\phi_i$ of the patterned article and thus to allow calibration of the polarizer only at three measurement angles avoiding a need for the calibration data interpolation.

There is a special case when the grating is oriented at a 45°-angle relative to the polarizer's axis ($\phi$=45°), and the diffraction efficiencies $R_0$ and $R_{90}$ are actually the same values. Hence, instead of three independent different measurement conditions, only two are unique. This problem can be overcome by calibrating the polarizer for at least one additional angle, e.g., (-45°), and thus four polarization states will be available for measurements: 0°, 90°, 45° and -45°. It is thus clear that even with four pre-selected angles, there might be grating angles in which the matrix of coefficients A has a large condition-number (defined as the ratio of its largest eigenvalue to its lowest eigenvalue, both in absolute values), indicating a high degree of non-uniqueness. The inventors have found that for the set of measurement angles $\beta\{-45°, 0°, 45°, 90°\}$, this occurs for angles of the form 22.5+45n where n=0, 1, 2, . . . .

From the standpoint of uniqueness of three selected measurement angles, the use of more than three pre-calibrated angles $\beta_i$ is preferred, and thus the higher uniqueness of the selected three measurements (at $\beta_1$, $\beta_2$ and $\beta_3$) can be achieved. For simplicity, let's consider that angles $\beta$ are accurate multiples of 15°, e.g., 0°, 15°, 30°, 45° and so on, until 180°. A simple algorithm for selecting these three angles from the pre-calibrated orientations is as follows:

$\beta_1$ is selected as the closest angle to the actual angle $\phi$ of the array;
$\beta_2$ is selected as $\beta_2=\beta_1+45°$;
$\beta_3$ is selected as $\beta_3=\beta_1+90°$.

If limiting the measurements to only four pre-selected angles is considered, it can be shown that the smallest condition number of the matrix A is achieved for the set of angles $\{0°, 65.2°, 90.4°, 116.9°\}$. For simplicity, such a set may be rounded to the following angles: $\{0°, 60°, 90°, 120°\}$. Since matrix coefficients do not depend on application, this set of angles is optimal for any application.

Figure 3:
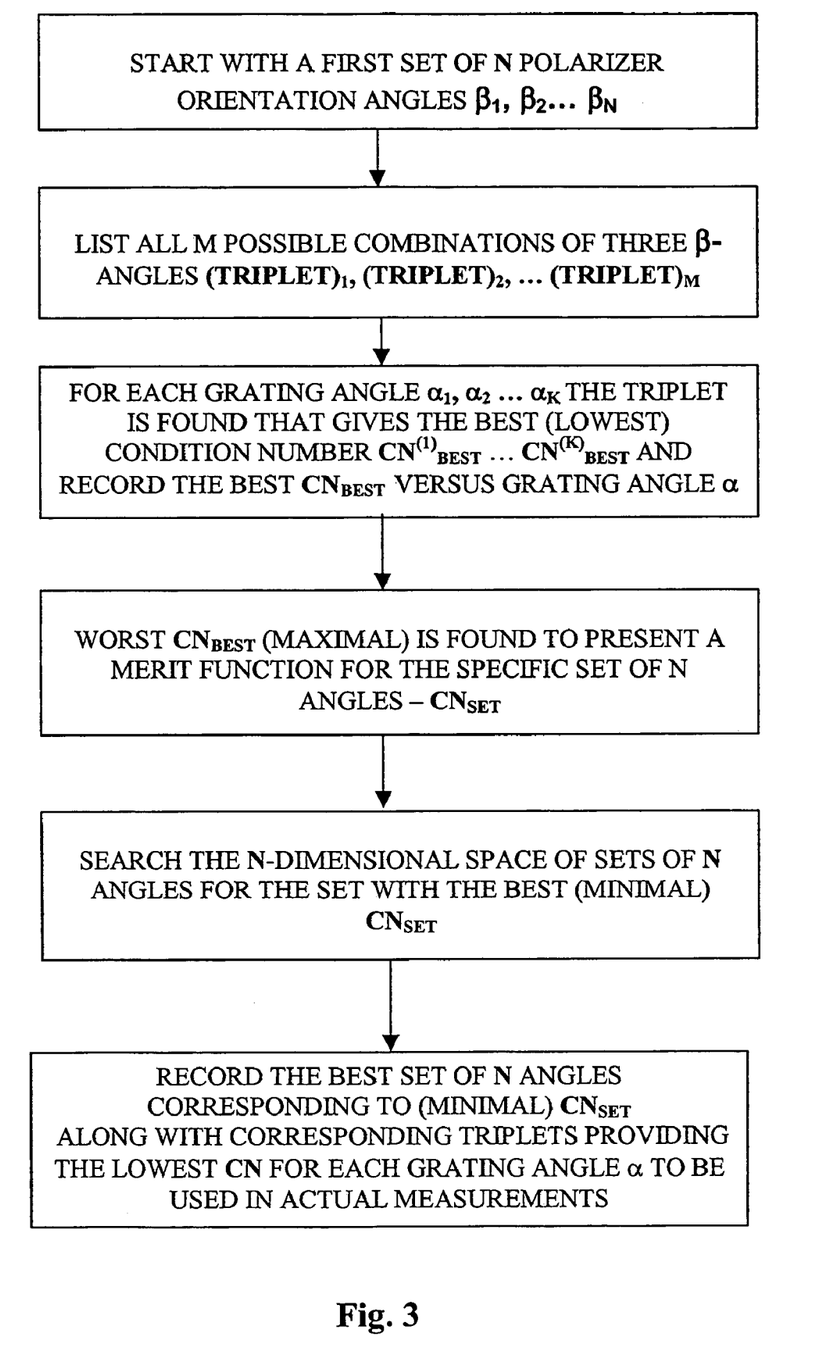
FIG. 3 exemplifies a calibration method of the invention for creating reference data indicative of an optimal set of angles from which angles for measurements are to be selected.

Referring to FIG. 3, there is exemplified a flowchart of a method of the invention showing the way of selecting the best set of N angles (for any number larger than 3) that can be found systematically. It makes use of the condition number CN (ratio of the largest eigenvalue and smallest eigenvalue) of the coefficients matrix A, defined above. Initially, a first, arbitrary set of N angles of polarizer orientation is selected, $\beta_1$, . . . $\beta_N$. All possible M combinations of 3 angles (triplets) from these N angles are defined, (triplet)$_1$, . . . , (triplet)$_M$. Then, for each grating angle $\alpha$ from a certain variety of K grating angles, $\alpha_1$, . . . , $\alpha_K$, the triplet that provides the best (minimal) CN value is found, namely $CN^{(1)}_{best}$, . . . , $CN^{(K)}_{best}$. Then, the worst value of $CN_{best}$, namely, the maximal value, is found to present the merit function, $CN^{(1)}_{set}$, for this first set of polarizer orientation angles. Then, a second set of N polarizer orientation angles is defined, $\beta_1, \ldots, \beta_N$, by slightly varying the angles of the first set, and similarly, a merit function, $CN^{(2)}_{set}$ for this second set of polarizer orientation angles is determined. This procedure is repeated Q times, and merit functions $CN^{(1)}_{set}, \ldots, CN^{(Q)}_{set}$ are found, which process actually presents searching for an N-dimensional space and characterizing this space by the minimal value of $CN^{(min)}_{set}$ that has its corresponding set of N polarizer orientation angles. The set of N angles defining this space of $CN^{(min)}_{set}$ presents the best set of angles for actual measurements on the article.

After the best set of N angles is found, the selection rules are determined for selecting 3 angles out of N for each possible grating angle $\beta_i$ which has been recorded during the above calibration procedure. Now, during the actual measurements with a given grating angle $\alpha$, the corresponding best triplet of polarizer orientation angle is used, utilizing the above reference data.

Figure 4A:
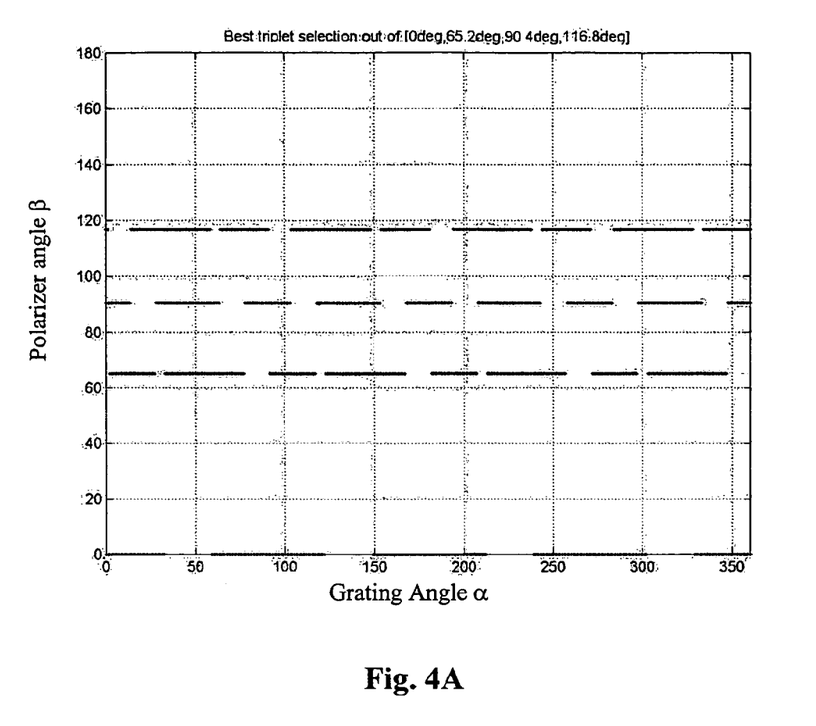
FIGS. 4A-4B and 5A-5B exemplify the technique of the present invention for selecting three polarizer angles for measurements from four optimal angles.
Figure 4B:
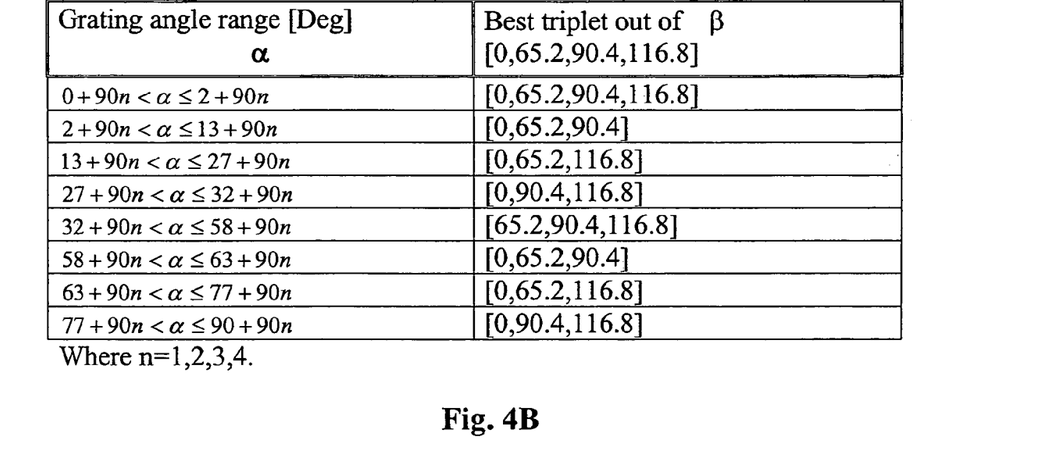
Figure 5A:
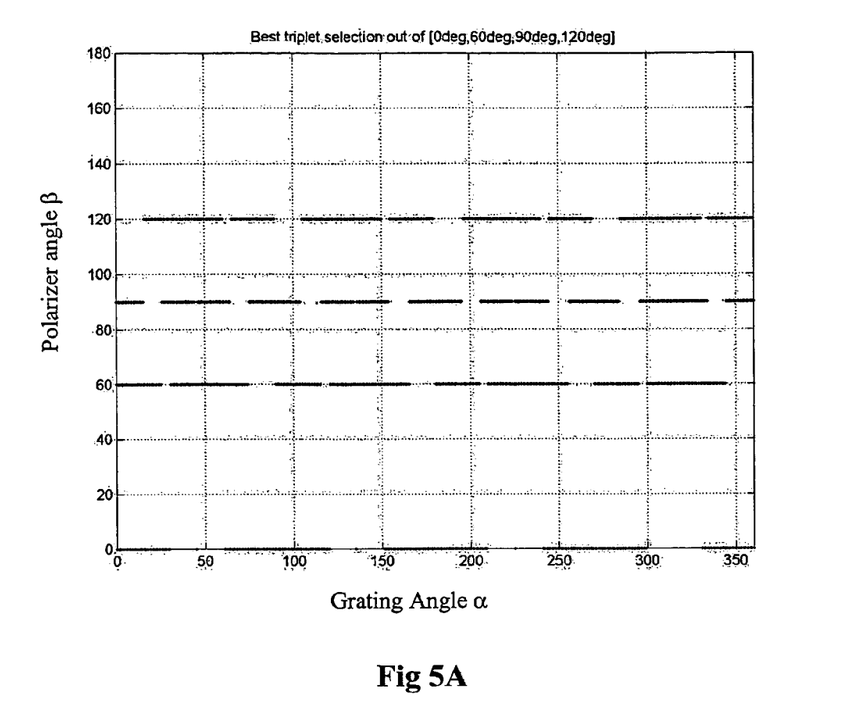
Figure 5B:
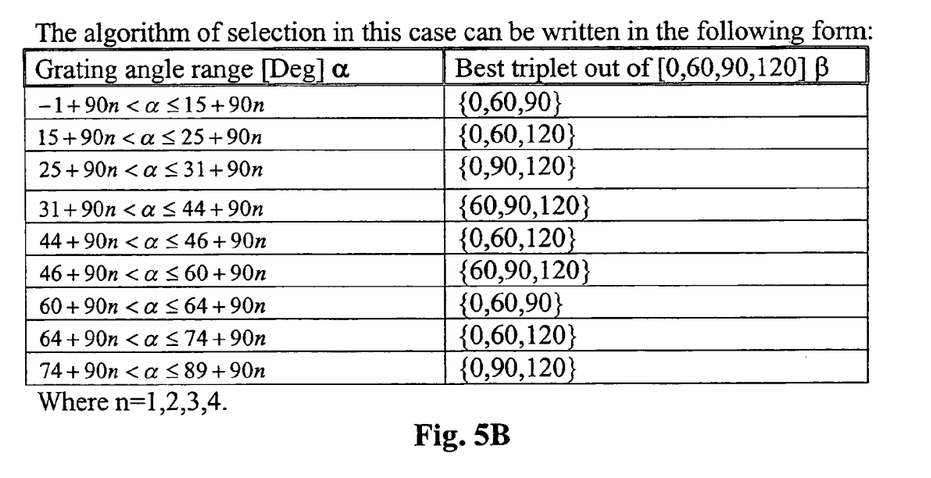

Reference is made to FIGS. 4A-4B and 5A-5B exemplifying the technique of the present invention for selecting three polarizer angles for measurements from four optimal angles. FIG. 4A shows four graphs that correspond to, respectively, the selected angular orientations $\beta_1, \beta_2, \beta_3$ and $\beta_4$. Thus, each orientation of the grating (x-axis) has its three optimal corresponding orientations of the polarizer (y-axis), at which the measurements are to be taken. FIG. 4B is a table showing the best three angles out of the four angles for every possible grating angle:

For simplicity, such a set may be rounded to the following angles: $\{0°, 60°, 90°, 120°\}$. This is illustrated in FIGS. 5A-5B.

Figure 6:
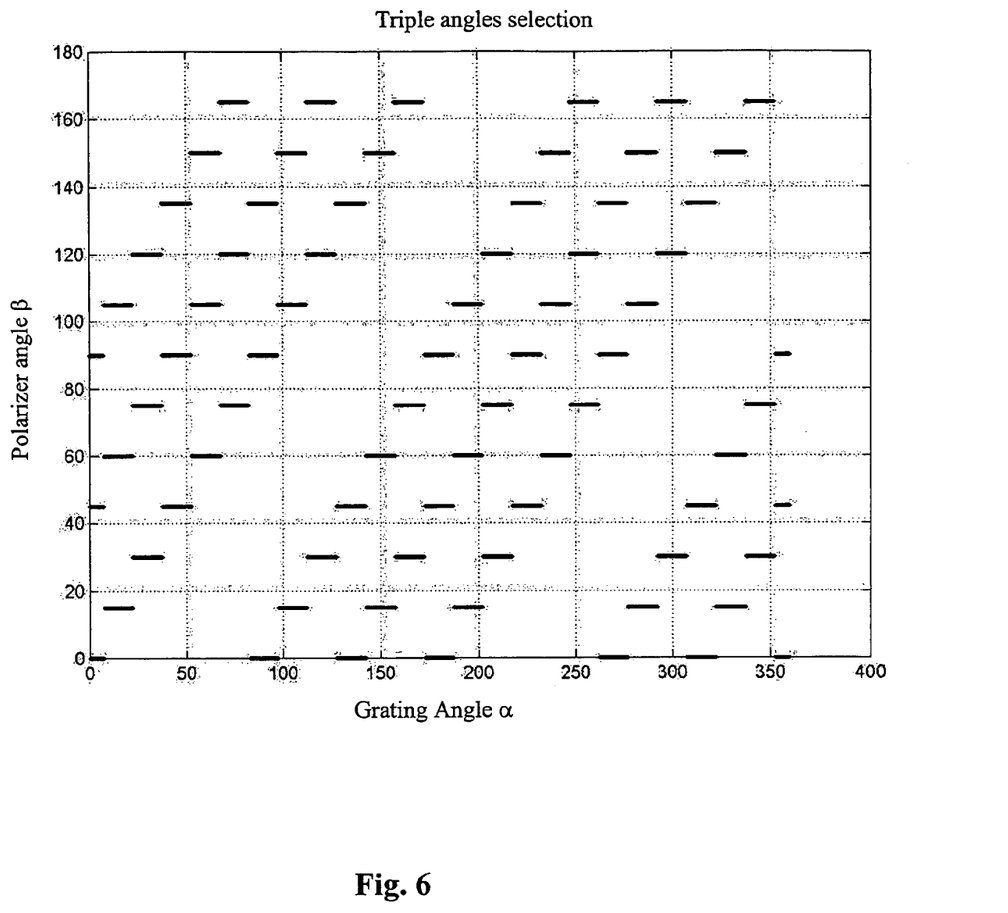
FIG. 6 graphically exemplifies the principles of the present invention for selecting three optimal angular orientations of a polarizer for measurements in each measurement site of the article.

The result of selecting three polarizer angles for each angle $\alpha$, according to the above algorithm, but for more than 4 selected polarizer angles is illustrated in FIG. 6. The figure shows an example of using three-angles selecting algorithm from pre-calibrated orientations: 0°, 15°, 30°, etc. (i.e., the polarizer rotation step of 15°). This figure shows the angular orientation $\beta$ of the polarizer (vertical axis) vs. the angular orientation of the grating, namely, the angle $\alpha$ between the line array axis and the zero-angle polarizer position (horizontal axis). Thus, each orientation of the grating has its three optimal corresponding orientations of the polarizer, $\beta_1$, $\beta_2$ and $\beta_3$, at which the measurements are to be taken.

Figure 7:
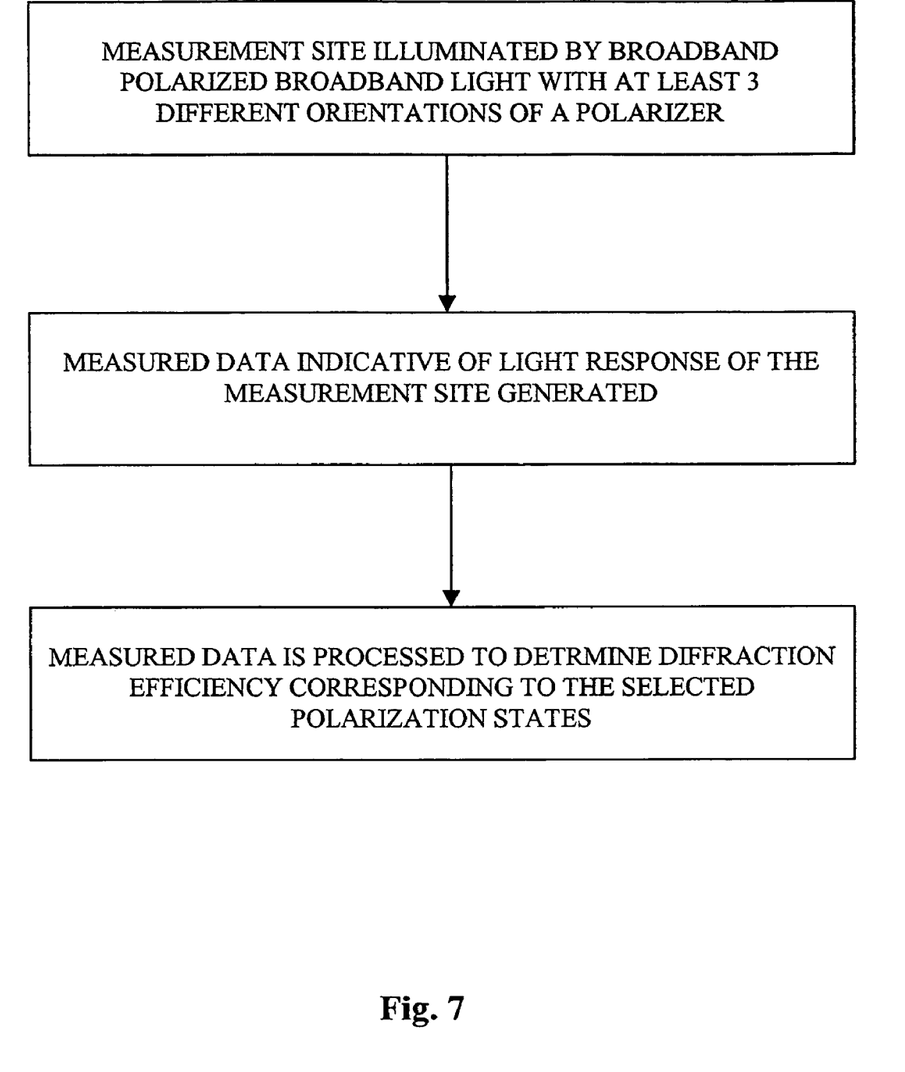
FIG. 7 illustrates a flow diagram of the main operational steps in a method of the present invention.

Referring to FIG. 7, there is illustrated a flow diagram of the main steps of a method of the present invention. Measurements are applied to a measurement site on the article using polarized broadband light (generally, a plurality of wavelengths) normal incident into the article. The measurements are taken with at least three different orientations of a polarizer at which the system was previously calibrated. A light response of the measurement site is detected. Measured data indicative of the detected light is processed to determine the diffraction efficiencies corresponding to the selected polarization states, thereby enabling determining the pattern parameters.

Examples of a method of the present invention for one measurement site will now be described with reference to FIGS. 8 and 9. The measurement system is calibrated for a pre-selected set of N polarizer orientations, which includes at least four polarizer angular orientations $\beta$. When the article (wafer) is loaded in the system, actual measurements are taken. In order to optimize the measurements, the following procedure is carried out: a grating-containing (patterned) site is selected for measurements; the grating orientation $\alpha$ ($\phi$) is determined; and based on this information the optimal three polarizer orientations $\beta_1, \beta_2$ and $\beta_3$ are selected from the calibration set $\beta_1, \beta_2, \ldots \beta_N$ (the set selected to be the best one during the above-described calibration procedure aimed at determining the reference data). Grating angular orientations $\phi_1, \phi_2$ and $\phi_3$ corresponding to the polarizer orientations $\beta_1, \beta_2$ and $\beta_3$ are defined based on information on orientation of the line array axis of the pattern. Preferably, angle $\phi_1 = \alpha$ being an angle between the line array axis and the zero-angle polarizer position $\beta_1$. It should be noted that this optimization procedure may be done off-line, e.g., as a recipe design step for semiconductor wafers. Measurements are applied to the article with the three selected polarizer orientations and diffraction efficiencies $R^{meas}(\phi_1)$, $R^{meas}(\phi_2)$ and $R^{meas}(\phi_3)$ are determined.

The further interpretation of the so-determined (measured) diffraction efficiencies $R^{meas}(\phi_1)$, $R^{meas}(\phi_2)$ and $R^{meas}(\phi_3)$ is based on a suitable theoretical analysis of light diffraction on gratings, for example, based on RCWT. The standard RCWT equations are formulated so as to provide such output parameters as $R_{TE}$, $R_{TM}$ and $\delta$ (phase shift). The theoretical analysis utilizes a predefined model based on the parameters of pattern (e.g., profile, period, tilt, etc.).

It should be understood that a certain inconvenience is caused by that the measured parameters $R(\phi_1)$, $R(\phi_2)$ and $R(\phi_3)$ are different from the output parameters of the calculation which are usually $R_{TE}$, $R_{TM}$ and $\cos \delta$, because the mostly used data interpretation method is based on iterative calculation of theoretical parameters and comparing them with the measured parameters: when the measured and calculated parameters are equal within predefined measurement errors, the optical model used for calculating the theoretical output parameters provides the required information about the line profile. Such inconvenience can be avoided. The preferred way for this is to transform the calculated parameters $R_{TE}$, $R_{TM}$ and $\cos \delta$ for each orientation $\beta$ using the equation (1) above. Since the calculation accuracy is practically unlimited, such transformation will not induce any additional errors. After such transformation, the theoretical output parameters $R^{sim}(\phi_1)$, $R^{sim}(\phi_2)$ and $R^{sim}(\phi_3)$ will be compared directly to the measured parameters $R^{meas}(\phi_1)$, $R^{meas}(\phi_2)$ and $R^{meas}(\phi_3)$.

Figure 8:
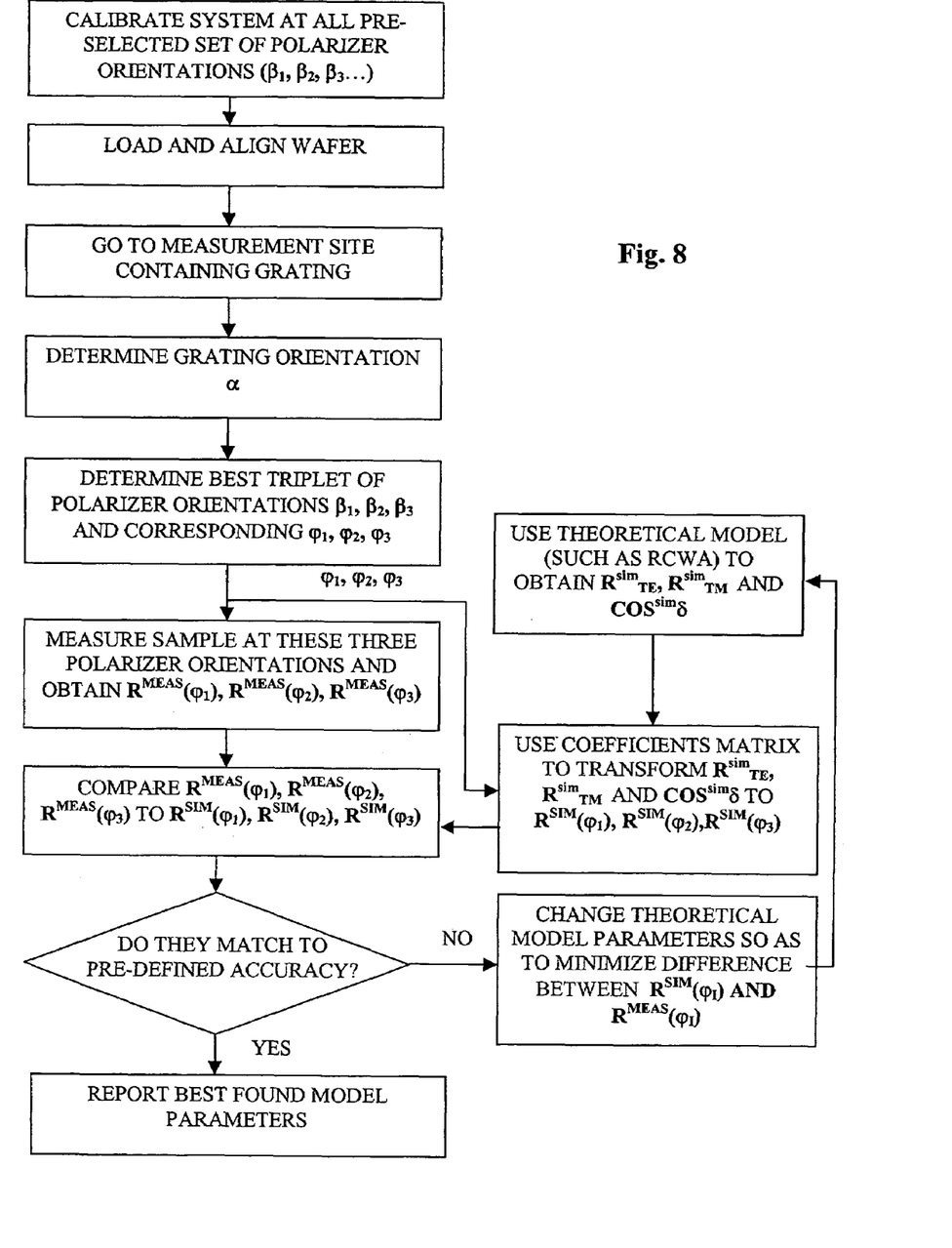
FIGS. 8 and 9 illustrate flow diagrams of two examples, respectively, of the method according to the invention.

According to the example of FIG. 8, the data indicative of the optimized polarization orientations set is processed using coefficient matrix to transform $R_{TE}$, $R_{TM}$, and $\cos(\delta)$ (determined using RCWT) to $R^{sim}(\phi_1)$, $R^{sim}(\phi_2)$ and $R^{sim}(\phi_3)$ by the equation (1) for each $\phi$. Then, measured values $R^{meas}(\phi_1)$, $R^{meas}(\phi_2)$ and $R^{meas}(\phi_3)$ are compared to $R^{sim}(\phi_1)$, $R^{sim}(\phi_2)$ and $R^{sim}(\phi_3)$. If these values satisfy a matching condition with a predefined accuracy, the measurements are accepted and are continued for a next site on the article. If no matching is detected, the model parameters are changed to minimize the difference, and new values of $R_{TE}$, $R_{TM}$, and $\cos(\delta)$ are determined.

There is another way of matching the measured and calculated parameters.

Figure 9:
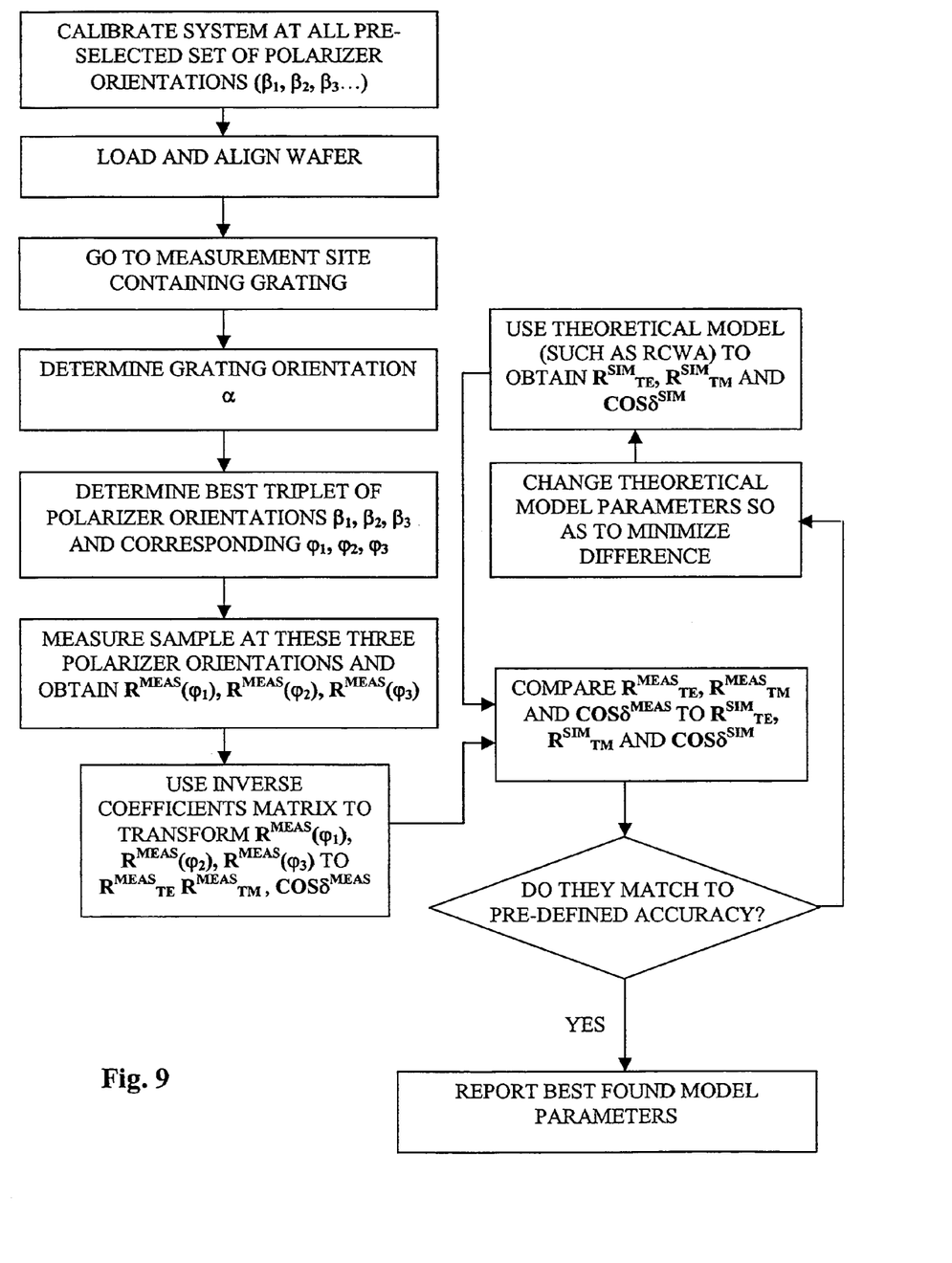

In the example of FIG. 9, the measured values $R^{meas}(\phi_1)$, $R^{meas}(\phi_2)$ and $R^{meas}(\phi_3)$ are processed using the matrix coefficients to determined the corresponding values of $R^{meas}_{TE}$, $R^{meas}_{TM}$, and $\cos(\delta)^{meas}$ by solving the equation (3). Then, the so-measured values $R^{meas}_{TE}$, $R^{meas}_{TM}$, and $\cos(\delta)^{meas}$ are compared to simulated (using RCWT) values $R^{sim}_{TE}$, $R^{sim}_{TM}$, and $\cos(\delta)^{sim}$. If the matching exists (with predefined accuracy), the measurement is accepted; if not, the model parameters are changed and new values of $R^{sim}_{TE}$, $R^{sim}_{TM}$, and $\cos(\delta)^{sim}$ are obtained.

Those skilled in the art will readily appreciate that various modifications and changes can be applied to the embodiments of the invention as hereinbefore exemplified without departing from its scope defined in and by the appended claims.

The invention claimed is:

1. A method for use in measuring/inspecting a patterned article, the method comprising applying optical measurements to a measurement site on the article by illuminating the measurement site with a plurality of wavelengths at substantially normal incidence of the illuminating light, detecting light returned from the illuminated site, and generating measured data indicative thereof, wherein the measurements are applied to the measurement site through a polarizer rotatable between its different orientations selected from a number of pre-calibrated orientations;
    wherein the measurements applied to the measurement site are carried out with the at least three different orientations of the polarizer selected from the at least four pre-calibrated orientations;
    wherein said at least three selected polarization orientations include two mutually perpendicular polarizations corresponding to the angular orientations β and (90+β), and at least one intermediate polarization orientation corresponding to the polarization vector orientation in between said mutually perpendicular polarization states.

2. The method of claim 1, wherein said at least one intermediate polarization corresponds to a (+45°) angular orientation.

3. The method of claim 2, wherein the intermediate polarizations include that corresponding to a (−45°) angular orientation.

4. The method of claim 1, wherein said at least one intermediate polarization corresponds to a (−45°) angular orientation.

5. The method of claim 1, wherein the at least three selected polarization orientations include angular orientations $\beta_1$, $\beta_2$ and $\beta_3$ spaced from each other by a certain step.

6. The method of claim 5, wherein said certain set of angles includes: {0°, 65.2°, 90.4°, 116.9°}.

7. The method of claim 5, wherein said certain set of angles includes: {0°, 60°, 90°, 120°}.

8. The method of claim 1, wherein the selected polarization orientations include at least one additional intermediate polarization orientation.

9. The method of claim 8, wherein the three selected polarization orientations include the polarization angular orientation closest to the given angular orientation of the pattern on the article under measurements with respect to a zero-angle of the polarization orientation.

10. The method of claim 1, comprising processing the measured data and determining diffraction efficiencies $R_{TE}$ and $R_{TM}$ for, respectively, linear polarization states of the illuminating light relative to the pattern on the article under measurements, and a phase shift between them, thereby enabling calculation of a diffraction efficiency $R(\phi)$ for any angular orientation $\phi$ of the polarizer relative to the pattern.

11. The method of claim 10, wherein the diffraction efficiency $R(\phi)$ is calculated as:

$$R_\phi = R_{TE} \cdot \cos^4\phi + R_{TM} \cdot \sin^4\phi + 2\sqrt{R_{TE} \cdot R_{TM}} \cdot \cos\delta \cdot \sin^2\phi \cdot \cos^2\phi$$

wherein $\phi$ is the angle between the grating and polarizer orientations, $R_{TE}$ and $R_{TM}$ are the measured diffraction efficiencies for said mutually perpendicular polarization orientations, and $\delta$ is a phase shift between the diffraction efficiencies $R_{TE}$ and $R_{TM}$.

12. The method of claim 11, comprising processing the measured data to determined measured values of diffraction efficiencies, $R^{meas}(\phi_1)$, $R^{meas}(\phi_2)$ and $R^{meas}(\phi_3)$ for the three different angular orientations $\beta_1$, $\beta_2$ and $\beta_3$.

13. The method of claim 12, comprising using a predetermined theoretical model based on parameters of the pattern and defining matrix coefficients as follows:

$$\begin{pmatrix} R(\varphi_1) \\ R(\varphi_2) \\ R(\varphi_3) \end{pmatrix} = \begin{pmatrix} \cos^4\varphi_1 & \sin^4\varphi_1 & \sin^2\varphi_1\cos^2\varphi_1 \\ \cos^4\varphi_2 & \sin^4\varphi_2 & \sin^2\varphi_2\cos^2\varphi_2 \\ \cos^4\varphi_3 & \sin^4\varphi_3 & \sin^2\varphi_3\cos^2\varphi_3 \end{pmatrix}$$

$$\begin{pmatrix} R_{TE} \\ R_{TM} \\ 2\sqrt{R_{TE}R_{TM}}\cos\delta \end{pmatrix}$$

wherein $R(\phi_{1,2,3})$ are the diffraction efficiencies for the angular orientations $\phi_{1,2,3}$, to determine theoretical values of $R_{TE}$, $R_{TM}$ and $\cos\delta$.

14. The method of claim 13, comprising using the matrix coefficients to transform the theoretical values $R_{TE}$, $R_{TM}$ and $\cos\delta$ to theoretical values of diffraction efficiencies $R^{sim}(\phi_1)$ $R^{sim}(\phi_2)$ and $R^{sim}(\phi_3)$.

15. The method of claim 13, comprising using inverse of the matrix coefficients to transform the measured values $R^{meas}(\phi_1)$, $R^{meas}(\phi_2)$ and $R^{meas}(\phi_3)$ to measured values $R^{meas}{}_{TE}$, $R^{meas}{}_{TM}$ and $\cos\delta^{meas}$.

16. The method of claim 15, comprising comparing the measured values $R^{meas}{}_{TE}$, $R^{meas}{}_{TM}$ and $\cos\delta^{meas}$ to the theoretical values of $R_{TE}$, $R_{TM}$ and $\cos\delta$, to determine whether they satisfy a matching condition with a pre-defined accuracy.

17. The method of claim 16, comprising varying the model parameters, upon detecting that the matching condition is satisfied.

18. The method of claim 12, comprising comparing the measured values $R^{meas}(\phi_1)$, $R^{meas}(\phi_2)$ and $R^{meas}(\phi_3)$ to the corresponding theoretical values $R^{sim}(\phi_1)$, $R^{sim}(\phi_2)$ and $R^{sim}(\phi_3)$, to determine whether they satisfy a matching condition with a pre-defined accuracy.

19. The method of claim 18, comprising varying the model parameters, upon detecting that the matching condition is satisfied.

20. The method of claim 1, wherein the pattern is an array of spaced-apart parallel regions.

21. The method of claim 20, wherein the pattern acts as a diffractive grating for the illuminating light.

22. A system for use in measuring/inspecting a patterned article, the system comprising:
    an illumination assembly configured and operated for producing illuminating light of a plurality of wavelengths;
    a detection assembly comprising a spectrometer for receiving light of different wavelengths and generating measured data indicative thereof;
    a light directing assembly configured for directing the illuminating light onto the article along an axis substantially perpendicular to the article and collecting light returned from the article along said axis and directing the collected light to the detection assembly, the light directing assembly comprising a polarizer assembly operated to be rotatable between its different orientations; and a control unit operable for receiving and processing the measured data, the control unit utilizing calibrated data indicative of an angular orientation φ of the pattern on the article under measurements and at least three pre-calibrated orientations of the polarizer, to thereby select the different polarizer orientations for measurements on each measurement site;

wherein said at least three selected polarization orientations include two mutually perpendicular polarizations corresponding to the angular orientations β and (90+β), and at least one intermediate polarization orientation corresponding to the polarization vector orientation in between said mutually perpendicular polarization states.

23. The system of claim 22, wherein said at least one intermediate polarization corresponds to a (+45°) angular orientation.

24. The system of claim 22, wherein said at least one intermediate polarization corresponds to a (−45°) angular orientation.

25. The system of claim 23, wherein the intermediate polarizations include that corresponding to a (−45°) angular orientation.

26. The system of claim 22, wherein the selected polarization orientations include at least one additional intermediate polarization orientation.

27. The system of claim 22, wherein the three selected polarization orientations include the polarization angular orientation closest to the given angular orientation of the pattern on the article under measurements with respect to a zero-angle of the polarization orientation.

28. The system of claim 22, wherein the control unit processes the measured data to determine diffraction efficiencies $R_{TE}$ and $R_{TM}$ for, respectively, linear polarization states of the illuminating light relative to the pattern on the article under measurements, and a phase shift between them, thereby enabling calculation of a diffraction efficiency R(φ) for any angular orientation φ of the polarizer relative to the pattern.

29. The system of claim 28, wherein the control unit calculates the diffraction efficiency R(φ) as:

$$R_\phi = R_{TE} \cos^4\phi + R_{TM}\sin^4\phi + 2\sqrt{R_{TE} \cdot R_{TM}} \cos\delta \cdot \sin^2\phi \cdot \cos^2\phi$$

wherein φ is the angle between the grating and polarizer orientations, $R_{TE}$ and $R_{TM}$ are the measured diffraction efficiencies for said mutually perpendicular polarization orientations, and δ is a phase shift between the diffraction efficiencies $R_{TE}$ and $R_{TM}$.

30. The system of claim 29, wherein the control unit processes the measured data to determined measured values of diffraction efficiencies, $R^{meas}(\phi_1)$, $R^{meas}(\phi_2)$ and $R^{meas}(\phi_3)$ for the three different angular orientations $\beta_1$, $\beta_2$ and $\beta_3$.

31. The system of claim 30, wherein the control unit utilizes a predetermined theoretical model to define matrix coefficients as follows:

$$\begin{pmatrix} R(\varphi_1) \\ R(\varphi_2) \\ R(\varphi_3) \end{pmatrix} = \begin{pmatrix} \cos^4\varphi_1 & \sin^4\varphi_1 & \sin^2\varphi_1 & \cos^2\varphi_1 \\ \cos^4\varphi_2 & \sin^4\varphi_2 & \sin^2\varphi_2 & \cos^2\varphi_2 \\ \cos^4\varphi_3 & \sin^4\varphi_3 & \sin^2\varphi_3 & \cos^2\varphi_3 \end{pmatrix} \begin{pmatrix} R_{TE} \\ R_{TM} \\ 2\sqrt{R_{TE}R_{TM}}\cos\delta \end{pmatrix}$$

wherein $R(\phi_{1,2,3})$ are the diffraction efficiencies for the angular orientations $\phi_{1,2,3}$, to determine theoretical values of $R_{TE}$, $R_{TM}$ and cos δ.

32. The system of claim 31, wherein the control unit operates to use the matrix coefficients to transform the theoretical values $R_{TE}$, $R_{TM}$ and cos δ to theoretical values of diffraction efficiencies $R^{sim}(\phi_1)$, $R^{sim}(\phi_2)$ and $R^{sim}(\phi_3)$.

33. The system of claim 32, wherein the control unit operates to compare the measured values $R^{meas}(\phi_1)$, $R^{meas}(\phi_2)$ and $R^{meas}(\phi_3)$ to the corresponding theoretical values $R^{sim}(\phi_1)$, $R^{sim}(\phi_2)$ and $R^{sim}(\phi_3)$, to determine whether they satisfy a matching condition with a pre-defined accuracy.

34. The system of claim 33, wherein the control unit, upon determining that the matching condition is not satisfied, operates to vary the model parameters, until the matching condition is satisfied.

35. The system of claim 31, wherein the control unit operates to use inverse of the matrix coefficients to transform the measured values $R^{meas}(\phi_1)$, $R^{meas}(\phi_2)$ and $R^{meas}(\phi_3)$ to measured values $R^{meas}{}_{TE}$, $R^{meas}{}_{TM}$ and cos $\delta^{meas}$.

36. The system of claim 35, wherein the control unit operates to compare the measured values $R^{meas}{}_{TE}$, $R^{meas}{}_{TM}$ and cos $\delta^{meas}$ to the theoretical values of $R_{TE}$, $R_{TM}$ and cos δ, to determine whether they satisfy a matching condition with a pre-defined accuracy.

37. The system of claim 36, wherein the control unit, upon determining that the matching condition is not satisfied, operates to vary the model parameters, until the matching condition is satisfied.

* * * * *